United States Patent [19]

Fujiwhara et al.

[11] 4,029,503
[45] June 14, 1977

[54] DIFFUSIBLE-DYE RELEASING TYPE DYES WHICH COUPLE TO FORM COLORLESS PRODUCTS

[75] Inventors: Mitsuto Fujiwhara; Ryosuke Sato, both of Hino, Japan

[73] Assignee: Konishiroku Photo Industry Co., Ltd., Tokyo, Japan

[22] Filed: May 7, 1975

[21] Appl. No.: 575,374

Related U.S. Application Data

[62] Division of Ser. No. 453,862, March 22, 1974, abandoned.

[30] Foreign Application Priority Data

Mar. 28, 1973 Japan .............................. 48-34469

[52] U.S. Cl. ...................... 96/29 D; 96/3; 96/5; 96/6; 96/9; 96/51; 96/56; 96/66.3; 96/77; 96/95; 96/99
[51] Int. Cl.$^2$ ...................... G03C 7/00; G03C 5/54; G03C 7/04; G03C 5/30
[58] Field of Search .................. 96/3, 29 D, 77, 51, 96/53, 56, 5–7, 9, 66.3, 99, 95, 100

[56] References Cited

UNITED STATES PATENTS

| | | | |
|---|---|---|---|
| 2,435,173 | 1/1948 | Bavley | 96/100 |
| 2,668,112 | 2/1954 | de Cat | 96/56.4 |
| 3,028,238 | 4/1962 | Puschel et al. | 96/9 |
| 3,142,565 | 7/1964 | Blout et al. | 96/3 |
| 3,227,550 | 1/1966 | Whitmore et al. | 96/3 |
| 3,255,001 | 6/1966 | Blout et al. | 96/3 |
| 3,297,441 | 1/1967 | Green et al. | 96/3 |
| 3,443,940 | 5/1969 | Bloom et al. | 96/3 |
| 3,628,952 | 12/1971 | Puschel et al. | 96/3 |
| 3,649,266 | 3/1972 | Chapman et al. | 96/3 |
| 3,841,880 | 10/1974 | Kertel | 96/100 |

*Primary Examiner*—David Klein
*Assistant Examiner*—Richard L. Schilling
*Attorney, Agent, or Firm*—Flynn & Frishauf

[57] ABSTRACT

A diffusible-dye releasing type dye consisting of a radical which reacts with an oxidation product of a color developing principal agent in a color development process to yield a substantially colorless compound and a dye residue carrying water-soluble radicals. Its photographic uses are also disclosed.

24 Claims, No Drawings

DIFFUSIBLE-DYE RELEASING TYPE DYES WHICH COUPLE TO FORM COLORLESS PRODUCTS

This is a division, of application Ser. No. 453,862, filed Mar. 22, 1974, now abandoned.

This invention relates to a diffusible-dye releasing type dye, and further relates to its photographic uses. In particular, this invention relates to a dye for photographic use which itself has a color and is capable of yielding a diffusible dye in a color development process and to a novel photographic process employing said dye.

Heretofore, as a diffusible-dye releasing type dye for photographic use, there has been known only a certin kind of a so-called DDR Coupler (Diffusible Dye Releasing Coupler). A representative of such DDR Coupler is made of combining a compound known as a photographic coupler and a diffusible-dye residue at the active position of the former in which position the former compound reacts with an oxidation product of a color developing principal agent. Since these DDR Couplers release diffusible dyes which correspond to densities of images, these are applied to a photographic process employing a diffusion transfer process. Further, it is known that, in view of the fact that this DDR Coupler itself has color and is capable of releasing a diffusible-dye at the above-mentioned active position, the Coupler is employed in a conventional photographic negative-positive process whereby the amendment of a finally obtained image is carried out. Said amendment is based upon a so-called masking system.

Yet, in order to obtain a positive image in an image receiving material in the diffusion transfer process employing such DDR Coupler, it is necessary to use a direct-positive type photosensitive material as a photosensitive material to be used together with the coupler. In this case a complicated manufacturing process and required accuracy of the manufacturing conditions cost much, and, in addition, such photographic capacities as sensitivity and resolving power are unsatisfactory. The negative image obtained on the photosensitive material which is combined to the image receiving material cannot be practically utilized because the inherent image of the DDR Coupler is mixed thereon with the image formed by the reaction of the coupler with an oxidation product of the color developing principal agent employed. This is another defect of the DDR Couper.

In case such DDR Coupler is employed together with a usual photographic coupler as a masking agent, selection of the coupler residue of the DDR Coupler molecule and determination of the amount of the Coupler ought to be effected carefully. The selection of the coupler residue is effected in order to bring about the same color as the color yielded from the conventional coupler for the purpose of adjusting a color balance of the obtained color image. Therefore, it is extremely difficult to employ this practically.

Accordingly, an object of this invention is to provide a diffusible-dye releasing type dye for photographic use not having the above-mentioned defects.

A further object of this invention is to provide a diffusion transfer process employing said dye.

Another object of this invention is to provide a photosensitive composition for photographic use.

Other objects of this invention will be apparent from the contents of the specification hereinafter disclosed.

The diffusible-dye releasing type dye according to this invention is represented by the following general formula (I), and yields a diffusible dye along with a substantially colorless compound in the color development process;

General formula (I)

A — D in which A represents a radical which reacts with an oxidation product of a color developing principal agent in a color development process to yield a substantially colorless compound, and D represents a dye residue carrying water-soluble radicals.

Since the above-mentioned dye may release a diffusible-dye and simultaneously yield a substantially colorless compound in a color development process, the obtained images on the receiving material and on the photosensitive material may advantageously be utilized both where employed, for example, in a diffusion transfer process.

The diffusible-dye releasing type dye of this invention reacts in a color development process with an oxidation product of a color developing principal agent (for instance, the oxidation product formed according to the amount of a developed silver of the photosensitive material) by the radical A to give a colorless compound, when the radical D forms a diffusible dye by elimination.

The radical A may preferably be a radical having an active methylene radical in the position to which radical D is connected. The radical which further has a radical capable of activating said active methylene radical in the inside position adjacent to said methylene radical may be particularly preferred.

The preferred radical A is concretely exemplified by the radicals having the general formulae (II) and (III) set forth below.

General formula (II)

$$R-CH- \atop | \atop Y$$

General formula (III)

in which Y represents hydrogen, halogen, an alkyl radical, an aryl radical, a heterocyclic radical, —O-$R_1$ ($R_1$ is an alkyl radical, an aryl radical, a heterocyclic radical, an acyl radical or —$SO_2$-$R_2$ ($R_2$ is an alkyl, aryl or heterocyclic radical)) or —$COOR_3$ ($R_3$ is an alkyl radical), R represents —CO-$R_4$ ($R_4$ is hydrogen, hydroxyl, —$R_o$, —$OR_o$, —$N(R_o)_2$, —$NH_2$ or —$NHR_o$),

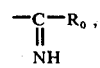

—$SO_2$-$R_5$ ($R_5$ is hydrogen, —$R_o$, —$OR_o$ or —$N(R_o)_2$), —SO-$R_5$ ($R_5$ is the same as above), —CH or —$N(R_6)_3$ ($R_6$ is hydrogen or —$R_o$), wherein $R_o$ is an aliphatic, aryl or heterocyclic radical and, in case there are two or more $R_o$s in the one radical, two of these $R_o$s may together form a nitrogen-containing heterocyclic ring, and Z represents a group consisting of atoms required in the formation of a carbon-cyclic or heterocyclic ring.

In the above description concerning the general formulae (II) and (III), the preferred radicals are exemplified as follows.

The alkyl radical may preferably have carbon atoms of up to 18, and may carry substituents such as halogen, a hydroxyl radical, an alkoxy radical and the like. In the radical Y, the alkyl may be a cyclic alkyl radical such as a cycloalkyl radical or may carry an aryl radical, for instance, an aralkyl radical. The aryl radical may preferably be a phenyl or naphthyl radical which may be substituted with a hydroxyl radical, halogen, a nitrile radical, an alkyl radical such as methyl or an alkoxy radical such as methoxy. The heterocyclic radical may have members of 5 to 6, and may be, for instance, a heterocyclic radical comprising one or more of hetero atoms such as N, O, S, Se and the like. The heterocyclic radical may be a condensation compound of a benzene ring, a naphthalene ring and the like, and may preferably be exemplified by radicals derived from a benzoxazole ring, a benzothiazole ring, a pyridine ring, a furan ring, a thiophene ring, imide succinate, imide phthalate, hidantoin, urazol and their derivatives. In particular, the heterocyclic radical of the radical Y may preferably be a benzoxazole ring, a benzothiazole ring, imide succinate, imide phthalate, hydantoin, urazol or their derivatives. The heterocyclic radical of $R_o$, $R_1$ or $R_2$ may preferably be pyridine, furan, thiophene or their derivatives. The acyl radical is represented by $-CO-R^1$ in which $R^1$ may preferably be the above-mentioned alkyl or aryl radical. The aliphatic radical may preferably be an unsaturated olefinic aliphatic radical having carbon atoms of up to 18 which may carry substituents. The nitrogen-containing heterocyclic ring made of two of $R_o$s of the above formula may preferably be a nitrogen-containing heterocyclic radical having members of 5 to 6, and may be exemplified by a piperidine ring, a pyrrolidine ring and a morpholine ring.

The carbon-cyclic ring and heterocyclic ring comprising Z may preferably be exemplified by the compound represented by the following formula (IV):

General formula (IV)

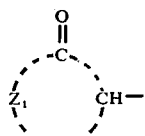

in which $Z_1$ represents a group consisting of atoms required in the formation of a carbon-cyclic or heterocyclic ring.

The carbon-cyclic ring may be a saturated or unsaturated 5 – 7 membered ring, and more concretely, for instance, cyclopentanone, cyclohexanone or cyclohexenone. This carbon-cyclic ring may embrace one carrying one or more substituents such as alkyl, aryl, alkoxy and/or aryloxy radicals and/or halogen (these radicals are the same as exemplified above) or may form a condensation ring in suitable positions, and may be exemplified by indanone, benzocyclohexenone or benzocycloheptenone. The heterocyclic ring may be a 5 – 7 membered ring containing one or more atoms of N, O, S, Se and the like, and can yield a substantially colorless compound when it reacts by its active methylene radical with an oxidation product of a color developing principal agent. This heterocyclic ring may be exemplified by piperidone, lactone, lactam, hydantoin and the like. Further, this ring may embrace one carrying one or more substituents such as alkyl, aryl and/or aryloxy radicals and/or halogen (these radicals are the same as exemplified above).

Said radical A may have a water-soluble dye residue such as the radical D, that is, it may have a dye residue such as the radical Y of the aforementioned general formula (II) and it may form a bis-structure by using the suitable above-mentioned radical as a connector. In the compound in which the radical A comprises a water-soluble dye residue, if there is another active methylene radical than the active methylene radical to which the radical D is connected, a water-soluble dye residue ought to be connected to the former active methylene radical. In other words, the water-soluble dye residue in the radical A may be readily released when subjected to a color development to let the remaining radical form a substantially colorless compound. In addition, the radical A may preferably carry a radical capable of bringing about a diffusion preventing property, and may preferably be not diffusible both before and after a color development.

The radical D of the aforementioned general formula may be released from the radical A when subjected to a color development and is a dye residue carrying a water-soluble radical. The water-soluble radical may be $-SO_2H$, $-SO_3M$ (M is a cation such as an ammonium ion or an alkali metal ion, e.g., a sodium or potassium ion), $-COOH$ or $-COOM$ (M is the same as the above) and preferably be an acidic one. The dye residue may preferably have a readily released radical in its end to which the radical is to be connected, and it may be exemplified by $-O-$, $-S-$, $-Hg-$, $-N=N-$, a tertiary nitrogen and the like. Representatives of dyes providing these dyes residues may be azo, azomethine, indoaniline, indophenol and anthraquinone dyes. Furthermore, said dye residue may contain the radical A in such manner that a bis-structure made of more than two of the radical A is formed. In this case, the radical A contained in the dye residue ought to be connected with the active radical to the dye residue.

Representatives of the compound having the general formula (I) which can yield a diffusible dye along with a colorless compound in a color development may concretely be set forth below.

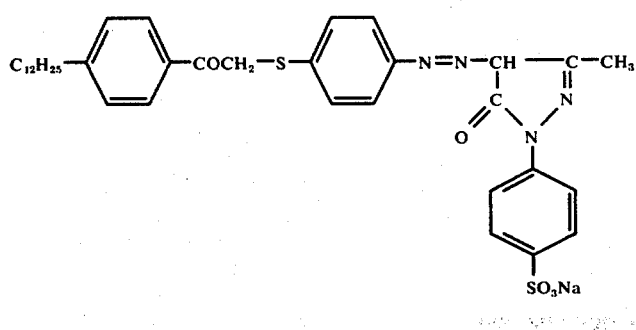
(1)
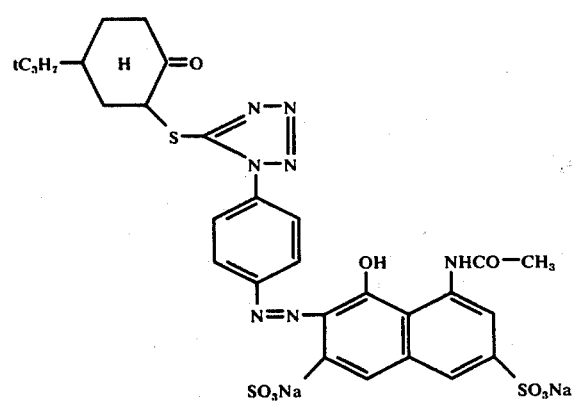
(2)
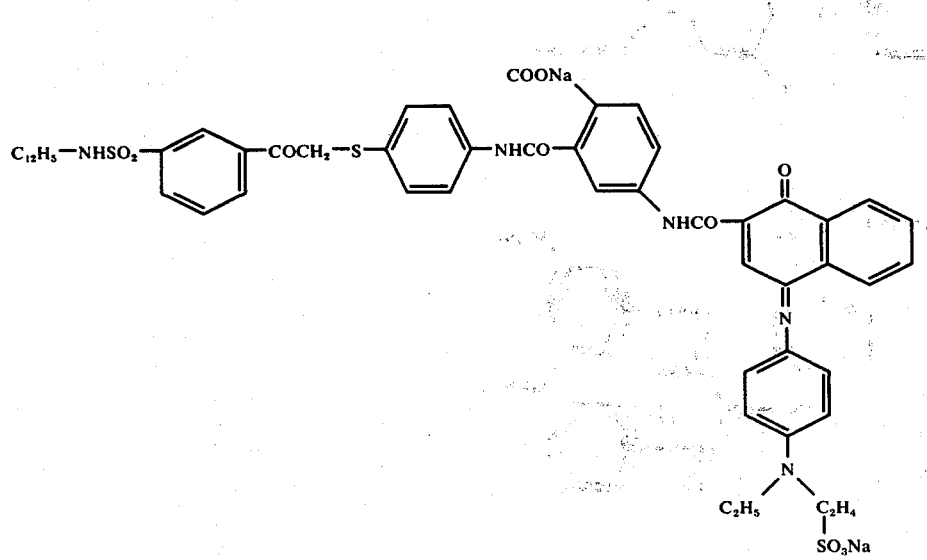
(3)
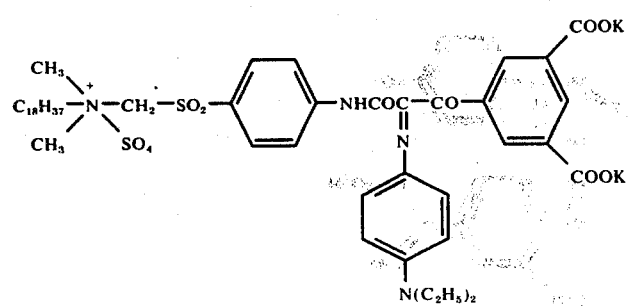
(4)

(5)
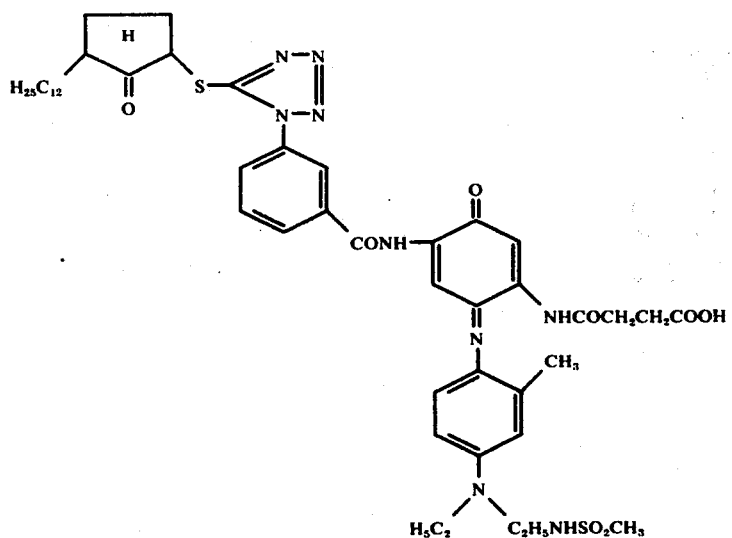
(6)
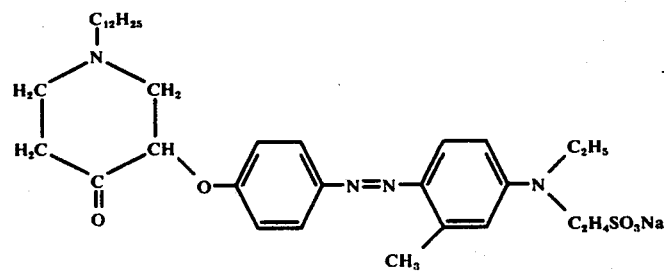
(7)
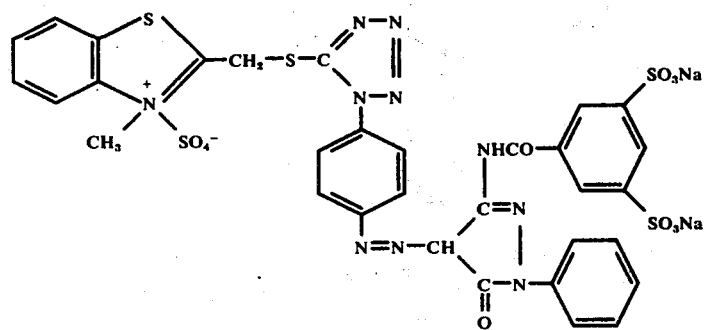
(8)
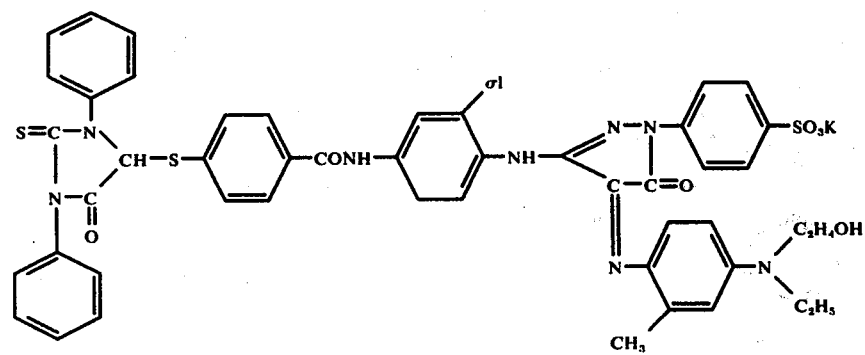

-continued
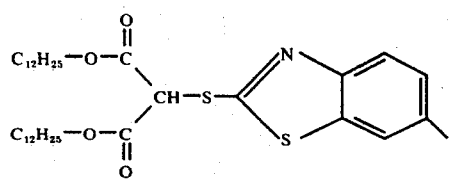
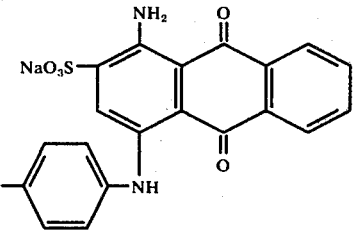
(9)
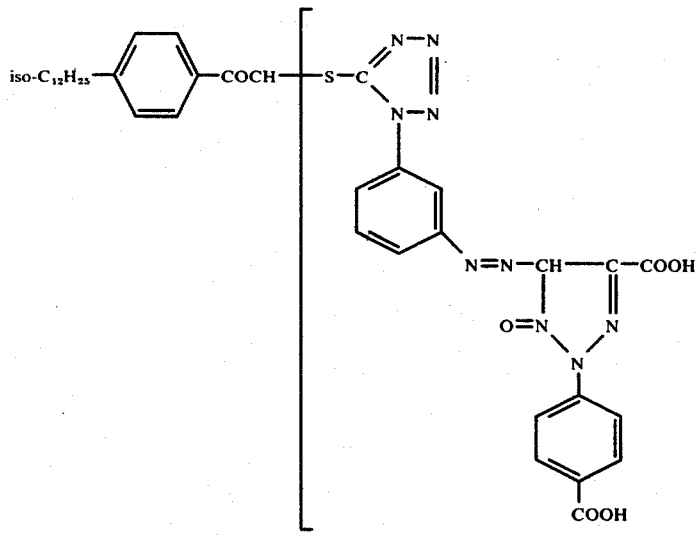
(10)
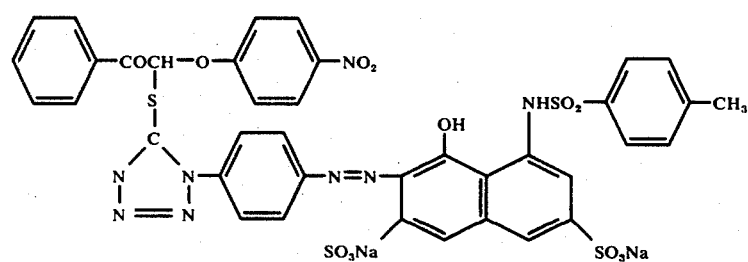
(11)
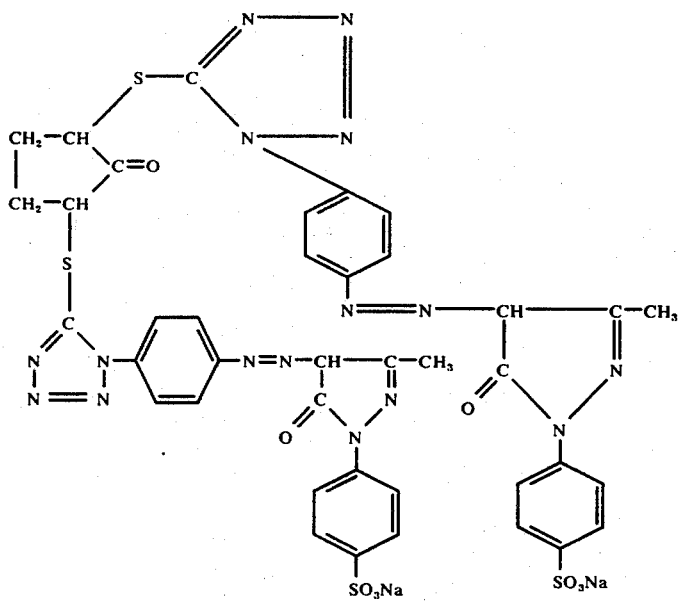
(12)
All of the above-exemplified compounds except the exemplified compounds (5) and (10) have decomposition points of more than 270° C. The decomposition point of the exemplified compound (5) is 210° C and that of the exemplified compound (10) is 193° – 197° C. The inherent color of each of the above-mentioned exemplified compounds is listed in the following Table 1.

Table 1

| Exemplified compound | Color |
|---|---|
| (1) | Yellow |
| (2) | Magenta |
| (3) | Cyan |
| (4) | Yellow |
| (5) | Cyan |
| (6) | Yellow |
| (7) | Yellow |
| (8) | Magenta |
| (9) | Blue |
| (10) | Yellow |
| (11) | Red |
| (12) | Yellow |

The compounds having the aforementioned general formula (I), which are concretely exemplified above, which can yield a diffusible dye along with a substantially colorless compound in a color development, and for this reason these have excellent properties as a diffusible-dye releasing type dye for photographic use. In case these are employed in a diffusion transfer process, the images formed on an image receiving material and on a photosensitive material are both adopted in practice. Furthermore, in case these are used in a masking system, these do not give any harmful effect on the obtained images. Thus, since the image remaining in the area after releasing a diffusible dye in a color development can be also utilized, these dyes can be employed in a novel photographic process. For instance, in case these dyes are employed together with a negative-type silver halide emulsion, there may be directly obtained a positive colored image on the photosensitive material. For this reason, a conventional negative-type silver halide emulsion may be utilized as a photosensitive material for obtaining directly a positive image. Therefore, the process for the manufacture employing the dye of the present invention is simpler than that employing conventional direct positive-type photosensitive materials.

As described above, the diffusible-dye releasing type dye for photographic use of the present invention have a lot of various advantages and wide applicability so that it is very useful in a photographic art.

Furhermore, a certain kind of the diffusible-dye releasing type dye for photographic use of the present invention such as the exemplified example (2), (5), (7), (9), (10), (11) or (12), yields a diffusible dye in a color development which shows a capacity in controlling a silver development in addition to the above-mentioned various merits. These mean that the present dye further has an excellent characteristic in improving sharpness of the images obtained in the color reproduction and also improving fineness of the images. Therefore, the use of two kinds of the compounds, a combination of a conventional coupler and a certain diffusible-dye releasing type dye for photographic use of the present invention (the dye which releases a diffusible dye having the power in controlling the development in a color development as mentioned above) can improve some photographic characteristics as same as or more than the use of three kinds of the coupler, a combination of a conventional coupler, DDR Coupler and so-called DIR Coupler (which is a coupler releasing a development inhibiting agent in a development process). In the above, the conventional coupler means a coupler being substantially colorless as such and yielding a color in a color development. For this reason, the use of the compound of the present invention can reduce the harmful effect of a silver halide emulsion which is together employed more than the use of the latter combination of the three couplers. Moreover, if a diffusible-dye releasing type dye which can release higher concentration of the diffusible dye is employed, the amount of the dye needed may substantially be reduced. This means that a small amount of the dye can give an enough masking effect. It is one of the further advantages that an adequate combination of the present compound and a conventional coupler can easily be determined because the compound obtained by the coupling reaction with the oxidation product of the color developing principal agent is colorless.

Particularly useful diffusible-dye releasing type dye for photographic use employed in a photosensitive material in order to obtain directly a positive image and in a diffusion transfer process may be a compound which releases the diffusible dye having no or little power in controlling the silver development, for example, the exemplified compounds (1), (3), (4), (6) and (8).

Representatives of the photographic process employing the diffusible-dye releasing type dye for photographic use of the present invention are concretely set forth below.

In a diffusion transfer process, a combination of an image receiving material and a photosensitive material is generally employed. The photosensitive material comprises at least one layer of a photosensitive layer on its support and the photosensitive layer is one consisting of gelatine - silver halide. The image receiving material comprises at least one layer of an image receiving layer. When the diffusible-dye releasing type dye for photographic use of the present invention is incorporated into the above-mentioned photosensitive layer and a color development is conducted by using a combination of the exposed photosensitive material and the image receiving material, the diffusible dye which is formed according to an amount of the developed silver in the area where the developed silver is formed is diffused into the image receiving layer to form an image according to the area where the developed silver of the photosensitive material is formed and to the amount of the developed silver thereon. The image on the image receiving material is obtained by separation of the photosensitive material and the image receiving material after the color development. In this case, there remaining on the photosensitive material the image being reversed from the image formed on the image receiving material, but the said remaining image cannot be utilized as such because the developed silver is present together. Yet, if the silver salts and the developed silver are removed out of the material by use of a fixing solution, a bleaching and fixing solution or a combination of a fixing solution and a bleaching solution, the color image remaining in the photosensitive material may advantageously be utilized as the image (a reversal image against the image on the image receiving material). In this procedure, a negative image is obtained on the image receiving material along with a positive image on the photosensitive material if a negative-type silver halide emulsion is employed as the photosensitive material. On the other hand, if a direct positive-type silver halide emulsion is employed as the photosensitive material, a positive image is obtained on the image receiving material along with a negative image on the photosensitive material. Accordingly, this process is very advantageous because a negative image and a positive image are both obtained in any of these procedures. It is also advantageous to employ, if required, a negative-type silver halide emulsion of which preparation is very easy. It is further merit of this process to be able to employ other images (for instance, the color image on the photosensitive material in the case of regarding the image on the image receiving material as a final one) than the color image originally employed as the original for printing so that this process is used for a one exposure — plural images system as well as for a one exposure — one image system.

The compounds of the present invention are effective as a positive-type photosensitive materials. For example, in case the diffusible-dye releasing type dye for photographic use of the present invention is incorporated into a negative-type silver halide photosensitive material and, after exposure, a color development and a bleaching and fixing (a combined process may be employed if desired) are conducted, the silver halide is removed into the solution to give finally a positive image. For this reason, the preparation and the treatment of the photosensitive material of this kind are extremely easy.

The compounds of the present invention are also effective as conventional negative-type photosensitive materials. For example, in case the present dyes are employed with any silver halide photosensitive materials for a negative and for a positive and a direct positive-type material, very excellent photographic properties can be obtained.

The amount of the present dye may be between about 0.07 and 0.7 mole, preferably about 0.1 and 0.4 mole, based on 1 mole of the silver halide, for obtaining a color image in any process, the amount of which is substantially similar to the amount for a convenional coupler. For the purpose of improving the property of a conventional coupler or improving other photographic properties by employing it with said coupler, the amount of the present dye may be between about 0.01 and 0.1 mole, preferably about 0.03 and 0.07 mole, based on 1 mole of the silver halide.

In any of the above processes, the photosensitive material which comprises two or more photosensitive layers, preferably three layers, each of which is sensitized in the wave length area different from each other and each of which contains the diffusible-dye releasing type dye of different colors is preferably employed for the purpose of obtaining the multi-colored image.

The photosensitive material used in any of the above processes consists of at least two members selected from the group of a support, a photosensitive layer, an intermediate layer, an underlying layer and a protective layer. The image receiving material used in the diffusion transfer process consists of at least two members selected from the group of a support, an image receiving material, a protective layer, an intermediate layer and a pH adjusting layer. In a certain diffusion transfer process the material consisting of two supports and photosensitive and image receiving layers placed between these supports in which at least one support is transparent and a layer capable of being made opaque is placed between the photosensitive layer and the image receiving layer is preferred. One of the above-mentioned photosensitive layer may consist of multiple layers of more than two which are exposed to the same wave length area. In the above, the layer being different to each other in sensitivity may be employed.

The binder for the formation of the layers may generally be gelatine, but other colloidal substances such as colloidal albumin cellulose derivatives and synthetic resins such as polyvinyl compounds, e.g., polyvinyl alcohol, may be employed alone or in combination with the gelatine. Further, acetyl cellulose of about 19 – 26% (by weight) of an acetyl content and a water-soluble ethanolamine cellulose acetate may be employed in combination with the above compounds.

The support for each layer may be paper, glass, cellulose acetate, cellulose nitrate, polyester, polycarbonate, polyamide, polystyrene or polyolefin.

The photosensitive layer may generally comprise silver halide such as silver chloride, silver iodide, silver iodobromide, silver chlorobromide or silver chloroiodobromide. These silver halides may be prepared by a neutral method, an ammonia method, an acidic method or the like depending upon the kind of the photosensitive materials. A simultaneously mixing method, a conversion emulsion method and the like may be employed. In the case of employing a mixed silver halide, a mixing ratio varies. For example, silver chloride may generally be the main one in the case of the type of a relatively lower sensitivity and fine particles. On the other hand, the content of the silver chloride is small in the case of the type of relatively higher sensitivity. In the case of using the direct positive-type silver halide, exemplified by Harshel reversal type and solarization type, an adequate fog is provided in advance by an optical or chemical method. These sensitizers are exemplified by an active gelatine, a sulfur sensitizer such as an allylthiocarbamide, thiourea or cysteine, selenium sensitizer, a reducing sensitizer such as stannous salt and polyamine, a precious metal sensitizer such as a gold sensitizer, concretely, potassium chloroaurite, potassium aurithiocyanate, potassium chloroaurate or 2-aurosulfobenzothiazol methochloride or a water-soluble salt of ruthenium, palladium, platinum, rhodium or iridium, concretely, ammonium chloropalladate, potassium chloroplatinate or sodium chloropalladate. Some of these sensitizers act as sensitizers or fog inhibiting agents depending upon the amount thereof. Further the sensitizers of these kinds are employed alone or in combination (for instance, the combination of a gold sensitizer and a sulfur sensitizer, a gold sensitizer and a selenium sensitizer and the like) so as to sensitize the silver halide chemically.

The silver halide can optically be sensitized in the desired area, and, for instance, by use of cyanine dyes such as zeromethine, monomethine, dimethine, trimethine dyes alone and in combination, the silver halide can be sensitized optically.

The photosensitive layer containing the silver halide may contain, depending upon the kind of the photosensitive material, and further, in case of using the diffusible-dye releasing type dye for photographic use of the present invention in combination with a conventional coupler, depending upon the kind of the layer, a magenta dye such as 5-pyrazolone, a yellow coupler comprising an active methylene radical placed between two carbonyl radical, a cyan coupler such as phenol and naphthol types. So-called 2 equivalent coupler and 4 equivalent coupler may be employed in the above materials.

The photosensitive layer and other constructive layers such as the intermediate, protective and underlaying layers and further the image receiving layer all may contain a variety of known additives for photographic use alone or in combination. Such additives may be exemplified by stabilizers such as mercury compounds, triazoles, azaindenes, zinc salts and cadmium salts, sensitizers such as quaternary ammonium and polyethylene glycols, membrane characteristics improving agents such as glycerine, dihydroxyalkanes, esters of ethylene bisglycolic acid and aqueous emulsions of polymers, membrane hardening agents such as formaldehyde, halogen substituted aliphatic acids, chloride disulfonate, bisaziridine and ethylene imines, spreading agents such as saponin, lauryl or oleylether of polyethyleneglycol, organic solvents such as high-boiling and low-boiling solvents, concretely, dibutyl phthalate, tricresyl phosphate, acetone, methanol, ethanol and ethyl cellusolve, antistatic agents, deforming agents, ultraviolet ray absorbing agents, fluorescent bleaching agents, anti-gliding agents, matting agents and halation or illusion inhibiting agents.

The diffusible-dyes releasing type dye for photographic use of the present invention which are employed in combination with the above-mentioned various components release diffusible dye in a color development for the photosensitive material. Representative of the color developing principal agent may be an aromatic primary amine developing principal agent, for instance, a p-phenylenediamine developing principal agent. Such a color developing principal agent may concretely be exemplified by N,N-diethyl-p-phenylenediamine, 2-amino-5-(N-ethyl-N-$\beta$-methylsulfonylamidoethyl)aminotoluene, 2-amino-5-(N-ethyl-N-$\beta$-hydroxyethyl)aminotoluene and N-ethyl-N-$\omega$-sulfobutyl-p-phenylenediamine. These are employed alone or in combination or, if desired, in combination with a black-and-white developing principal agent, for instance, hydroquinone. Further, these color developing principal agents are generally used together with alkali agents such as sodium hydroxide, ammonium hydroxide, sodium carbonate, sodium sulfate and sodium sulfite. The various additives contained in the color developing solution can be separated in combination form which is capable of conducting a color development directly. Either the color developing principal agents or the additives may be incorporated into either the photosensitive material or the image receiving material. For example, the color developing principal agent may be incorporated into the image receiving material, and the color development may be carried out with treatment of an alkaline solution.

The color developing principal agent becomes an oxidation type by the developing nuclea of the silver halide in the color development process, and then react with the aforementioned radical A of the diffusible-dye releasing type dye of the present invention to give a colorless compound.

The fixing agent, the bleaching agent, the bleaching-fixing agent and the like used for removing the silver chloride or the developed silver out of the photosensitive material may be employed together with different treating agents such as the stopping agent, the washing solution, the stabilizing solution and the like. The component for fixing may be the solution for the silver halide such as sodium thiosulfate and ammonium thiosulfate. The component for bleaching may be an alkali metal salt of ferricyanide, sodium or ammonium salt of ferric ethylenediaminetetraacetate and the like.

As described hereinbefore, a diffusible-dye releasing type dye of the present invention is characterized by yielding both of a colorless compound and a diffusible dye in a color development process. Therefore, this dye is, as mentioned above, more advantageous and more applicable than the conventional DDR Coupler.

The present invention is more concretely illustrated in the following examples, but these examples are not to limit the present invention.

SYNTHESIS EXAMPLE 1

Synthesis of the exemplified compound (1)

In 300 ml of a 10% hydrochloric acid was dissolved 41 g of p-dodecyl-$\alpha$-(p-aminophenylthio)acetophenone, and diazotation was conducted with 7.5 g of sodium nitrite under cooling. After decomposing excess nitric acid with sulfamine, the obtained diazonium salt was dropwith added under cooling to 1 liter of a 10% aqueous sodium hydroxide containing 25 g of 3-methyl-5-pyrazolone-1-(p-sulfophenyl) adjusted to pH 7 – 8. After completion of the addition, the obtained crystals were collected by filtration and recrystallized from 1.8 liter of 70% alcohol to give the aforementioned exemplified compound (1). Yield, 70%

SYNTHESIS EXAMPLE 2

Synthesis of the exemplified compound (3)

In 800 ml of pyridine was dissolved 78 g of n-dodecylsulfoamido-$\alpha$-(p-aminophenylthio)acetophenone. While this solution was maintained at a temperature in a range of 10 to 20° C, to this solution was added for about 20 minutes 119 g of 3-(4'-(4''-N-ethyl-N-$\omega$-sulfoethylaminophenylimino)-1'-naphthoquino-2'-carboamido)-phthalic anhydride, and this mixture was then heated to 50° – 60° C to complete the reaction. Upon the reaction mixture was poured into water and salted out with sodium sulfate, the desired compound was obtained. The compound thus obtained was collected by filtration and recrystallized from methanol. Yield, 65%

SYNTHESIS EXAMPLE 3

Synthesis of the exemplified compound (12)

In 500 ml of anhydrous chloroform was dissolved 93 g of 1-(p-(4-(1-p-sulfophenyl-3-methyl-5-pyrazolyl)azo)phenyl)-5-tetrazolylsulfenyl chloride, and to the solution was added 7.2 g of cyclopentanone. After stirring at room temperature for 24 hours, the chloroform and an excess of the cyclopentanone were removed by vacuum evaporation. The obtained yellow caramel was dissolved in a 0.1 N aqueous sodium hydroxide. After dissolving homogeneously, adjusting to pH 5 –7 and salting out with sodium chloride, there was obtained yellow amorphous crystals. The crystals were collected by filtration and recrystallized from acetonitrile to yield the desired substances as yellow plates.

EXAMPLE 1

A direct positive-type color photosensitive material was prepared by applying in the following order each composition to a triacetate base and drying.

1. In 30 ml of a 1 N aqueous sodium hydroxide was dissolved 8.0 g of the exemplified compound (5), and this solution was diluted with water into 100 ml. The resulting solution was added to 1 Kg of a red-sensitive silver iodobromide emulsion containing 70 g of silver iodobromide and then adjusted with an aqueous citric acid solution to pH 6.7.

2. The solution prepared in the above-mentioned manner by employing 8.0 g of the exemplified compound (8) was added to 1 Kg of a green-sensitive silver iodobromide emulsion containing 70 g of silver iodobromide and then adjusted to pH 6.7.

3. The solution prepared in the manner described in the above (1) by employing 8.0 g of the exemplified compound (1) was added to 1 Kg of a blue-sensitive silver iodobromide emulsion containing 70 g of silver iodobromide and then adjusted to pH 6.7.

The photosensitive materials prepared as above were subjected to wedge exposure by the use of blue light, green light and red light, and developed in the developer solution set forth below at a temperature of 20° C for 10 minutes.

| | | |
|---|---|---|
| N-Ethyl-N-hydroxyethyl-p-phenylenediamine sulfate | | 2.5 g |
| Anhydrous sodium sulfite | | 2.0 g |
| Hydroxylamine hydrochloride | | 1.0 g |
| Sodium carbonate (monohydrated) | | 82.0 g |
| Potassium bromide | | 2.0 g |
| Added water | into | 1 liter |

After the development, the procedure consisting of removal of silver, fixing, washing with water and drying was performed in a conventional manner.

The sample subjected to the blue-light exposure gave a sharp blue positive-image. The samples subjected to green-light and red-light gave sharp green and red positive-images, respectively.

As illustrated above, according to the present invention, the positive-image can be obtained directly by using a conventional negative-type silver halide emulsion. This, in other words, means that a direct positive-type photosensitive material can be prepared by a simple method. Therefore, it will be understood that the diffusible-dye releasing type dye of the present invention is useful for a direct positive type use.

EXAMPLE 2

In a mixture of 1.5 ml of dimethylformamide and 7.5 ml of triethylamine was dissolved 1.0 g of the exemplified compound (1), and to this solution was added 20 ml of a 5 % aqueous gelatine solution. After making the solution homogeneous, it was adjusted with an aqueous citric acid solution to pH 6.7. In a mixture of 10 ml of dibutyl phthalate and 30 ml of ethyl acetate was dissolved 7.0 g of the magenta coupler of 1-(2,4,6-trichlorophenyl)-3-(3-(α-(2,4 - di-t-amylphenoxyacetoamido))benzamido)-5-pyrazolone. This solution was added to a mixture of 30 ml of a 5% aqueous gelatine solution and 10 ml of 5% Alkanol B (available from Du Pont (E.I.) de Nemours & Co.) and the resulting mixture was emulsified. Both the emulsion of the examplified compound (1) obtained before and the magenta coupler emulsion obtained above were simultaneously added to 1 Kg of a green-light sensitive silver iodobromide emulsion. The resulting mixture was applied to the triacetate base and dried to give the sample.

The photosensitive material prepared as above was subjected to wedge exposure by the use of white light, and developed in the developer solution set forth below at a temperature of 24° C for 10 minutes.

| | | |
|---|---|---|
| Anhydrous sodium sulfite | | 2.0 g |
| N-Ethyl-N-β-methanesulfonamidoethyl-3-methyl-4-aminoaniline sulfate | | 5.0 g |
| Sodium carbonate (monohydrated) | | 50.0 g |
| Potassium bromide | | 0.9 g |
| Sodium hydroxide | | 4.0 g |
| Sodium hexametaphosphate | | 0.5 g |
| Benzyl alcohol | | 4.0 ml |
| Added water | into | 1 liter |

The bleaching and the fixing were conducted in a conventional manner.

The result shows that the blue density of the image was uniform over the exposed area and, therefore, the exemplified compound (1) can conveniently be utilized as a co-called masking agent for the magenta coupler.

EXAMPLE 3

This example shows that the fog-induction which occurred in a conventional colored coupler was reduced by using as the masking agent a compound of the present invention. Further, this shows that the process using this compound brings about the improvement of sharpness of the image consisting of particles.

In order to make a comparison with the photosensitive material employed in Example 2, the following procedure was performed.

In a mixture of 10 ml of dibutyl phthalate and 30 ml of ethyl acetate were dissolved both 1.2 g of 1-(2,4,6-trichlorophenyl)-3-(3-(α-2,4-di-t-amylphenoxyacetoamido)benzamido))-4-(4-methoxyphenylazo)-5-pyrazolone and 7.0 g of 1-(2,4,6-trichlorophenyl)-3-(3-(α-(2,4-di-t-amylphenoxyacetamido))-5-pyrazolone. The resulting solution was emulsified with 15 ml of 5% Alkanol B (available from Du Pont (E.I.) de Nemours & Co.) by means of a colloid mill. The obtained emulsion was added to 1 Kg of a green-light sensitive silver iodobromide emulsion. The mixture was applied to the triacetate base and dried to give the sample. The present sample as well as the sample obtained in Example 2 were both subjected to wedge exposure by the use of white light, and developed in the developer solution shown in Example 2 at a temperature of 24° C for 10 minutes. The bleaching and the fixing were conducted in a conventional manner.

The results shows that the fog value of the photosensitive material of this example is 0.25 and in contrast with 0.40 of that of the material of Example 2. This shows that a compound of the present invention is excellent as a masking agent. Further, the results showed that the photosensitive material of this example brought about superior particle property and sharpness to that of the material of Example 2.

EXAMPLE 4

The color photosensitive materials for the diffusion transfer process were prepared as follows.

1. Red-sensitive layer: In a mixture of 2 ml of dimethylformamide and 10 ml of triethylamine was dissolved 2 g of the exemplified compound (3), and this solution was added to 20 ml of a 5% gelatine solution. After sufficient mixing, the solution was adjusted with a 20% citric acid solution to pH 6.5.

The resulting solution was added to 100 g of a red-sensitive silver iodobromide emulsion, and applied to the triacetate support and then dried. The amount of the applied mixture was 15 mg as converted to a silver basis to the area of 100 cm$^2$ of the support.

19

2. Intermediate layer: A 10% gelatine solution for photographic use was applied to the above first layer in the dry thickness of 2 μ, and dried.

3. Green-sensitive layer: The solution prepared in the same manner described in above (1) by using 2 g of the exemplified compound (2) was added to 100 g of a green-sensitive silver iodobromide emulsion. The resulting mixture was applied to the above second layer in the amount of 15 mg as converted to a silver basis to the area of 100 cm², and dried.

4. Intermediate layer: A gelatinous intermediate was prepared on the above green-sensitive layer in the dry thickness of 2 μ in the same manner as in above (2).

5. Blue-sensitive layer: The solution prepared by using 2 g of the exemplified compond (1) in the same manner as in above (1) was added to 100 g of a blue-sensitive silver iodobromide emulsion. The resulting mixture was applied to the above fourth layer in the amount of 20 mg as converted to a silver basis to the area of 100 cm², and dried.

6. Uppermost layer (protective layer): The solution prepared by adding mucochloric acid to a 10% gelatine solution for photographic use in the amount of 1 mg of the former based on 100 ml of the latter was applied to the above fifth layer in the dry thickness of 2 μ, and dried.

The photosensitive material prepared as above was subjected to wedge exposures divided into blue, green and red wedges. The image receiving material was prepared by applying the gelatine solution containing 2 weight percent of trimethyllaurylammonium chloride to a transparent triacetate support and dried. These two materials were combined by means of a dry sheet.

| | | |
|---|---|---|
| Anhydrous sodium sulfite | | 2 g |
| Potassium bromide | | 1 g |
| Anhydrous sodium carbonate | | 40 g |
| 4-Amino-N-ethyl-N-β-hydroxyethyl-aniline hydrochloride | | 10 g |
| 10 % aqueous sodium hydroxide solution | | 22 ml |
| Added water | into | 1 liter |

The above-mentioned solution was introduced into between the combined materials. After standing at 22° C for 3 minutes under slight pressure, removal of the treating solution and transfer of the image were performed by squeezing strongly. Thus the negative color wedge image of yellow, magenta and cyan was obtained on the image receiving sheet. Another treatment of the photosensitive material using the silver removing solution and the fixing solution for a conventional color development gave a positive color wedge image of blue, green and red.

As described above, the color images of both negative and positive were easily obtained.

What is claimed is:

20

1. In a diffusion transfer process which comprises imagewise exposing a photosensitive material comprising a support and a silver halide photosensitive layer thereon containing silver halide grains and further comprising a dye image forming substance therein; developing the exposed photosensitive material in an aqueous developing solution in the presence of a color developing agent thereby to form a diffusible dye image corresponding to the imagewise exposure and derived from the dye image forming substance; and transferring the dye image from the photosensitive material to an image receiving layer superposed on the photosensitive material at least during the development whereby the dye image corresponding to the imagewise exposure is obtained in the image receiving layer, the improvement which comprises, as the dye image forming substance, a diffusible-dye releasing type dye having the formula:

$$R-\underset{Y}{\underset{|}{CH}}-D$$

in which D represents a dye residue carrying a water-soluble radical; Y represents hydrogen, halogen, an alkyl radical, an aryl radical, a heterocyclic radical, $-O-R_1$ or $-COOR_3$; $R_1$ is an alkyl radical, an aryl radical, a heterocyclic radical, an acyl radical or $-SO_2-R_2$; $R_2$ is an alkyl, aryl or heterocyclic radical; $R_3$ is an alkyl radical; R represents $-CO-R_4$,

$-SO_2-R_5$, $-SO-R_5$, $-CN$ or $-N(R_6)_3$; $R_4$ is hydrogen, hydroxyl, $-R_O$, $-OR_O$, $-N(R_O)_2$, $-NH_2$ or $-NHR_O$; $R_5$ is hydrogen, $-R_O$, $-OR_O$ or $-N(R_O)_2$; $R_6$ is hydrogen or $-R_O$; and $R_O$ is an aliphatic, aryl or heterocyclic radical, and when two or more $R_O$s are present in one radical, two of said $R_O$s can form together a nitrogen-containing heterocyclic ring, the diffusible-dye releasing type dye per se being non-diffusible and capable of coupling with the color developing agent in the aqueous developing solution in the presence of the exposed silver halide to split off D in the formula whereby the dye image is produced from D so split off, and the compound produced upon splitting off D being substantially colorless.

2. A diffusion transfer process of claim 1, in which a molar ratio of the silver halide and the diffusible-dye releasing type dye ranges from about 1 : 0.07 to about 1 : 0.7.

3. A diffusion transfer process of claim 1, in which a molar ratio of the silver halide and the diffusible-dye releasing type dye ranges from about 1 : 0.1 to about 1: 0.4.

4. A diffusion transfer process of claim 1, wherein said dye is selected from the group consisting of (1) 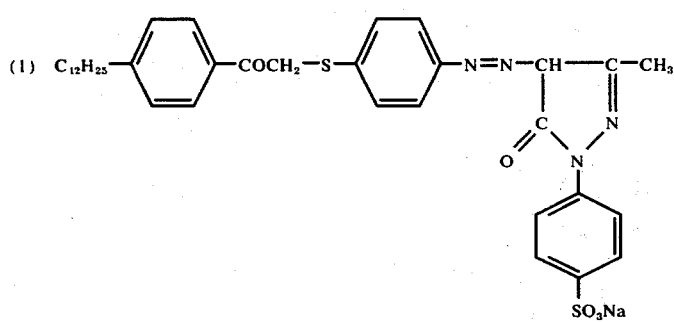
(2) 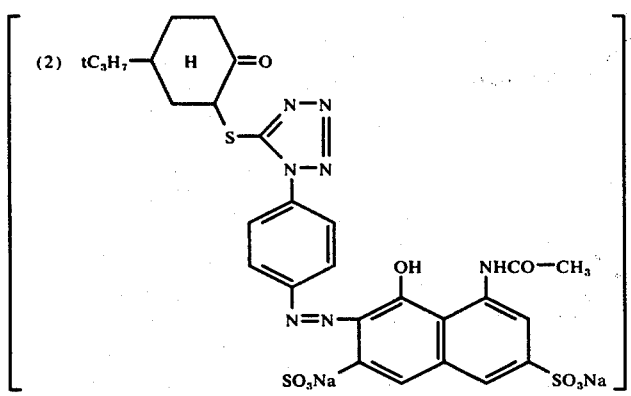
(3) 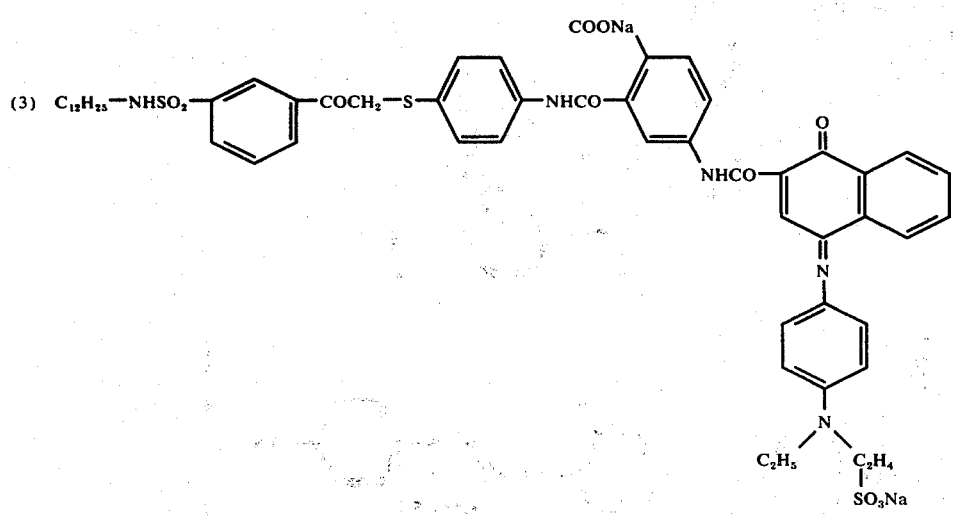
(4) 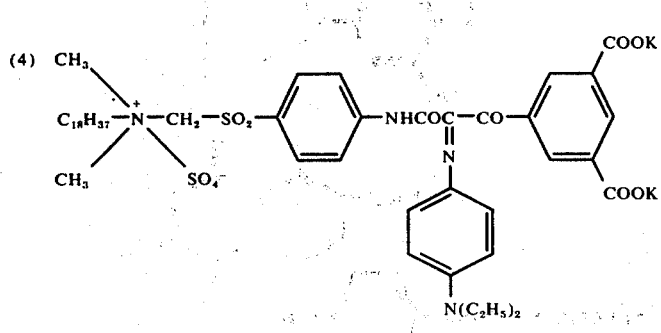

-continued
(5) 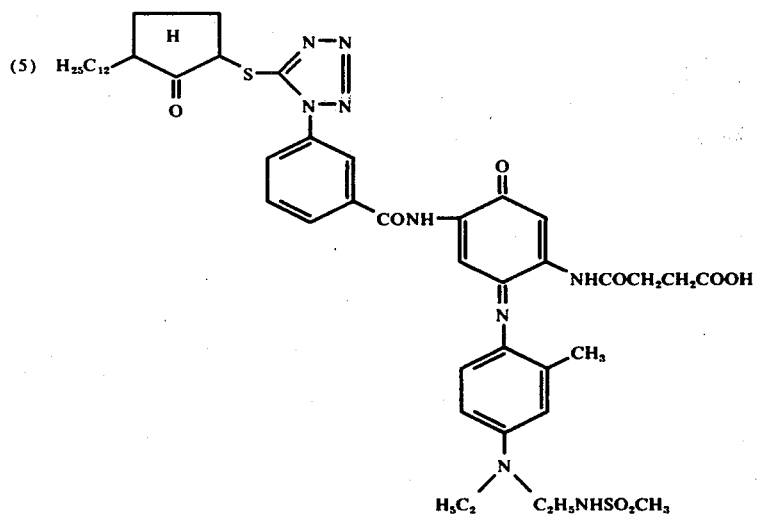
(6) 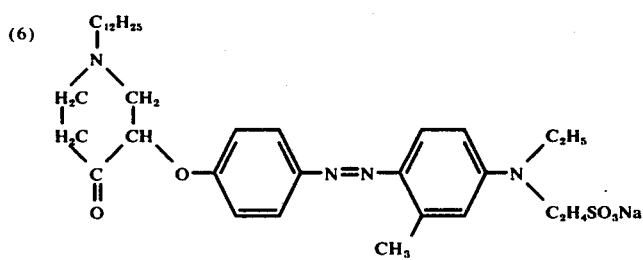
(7) 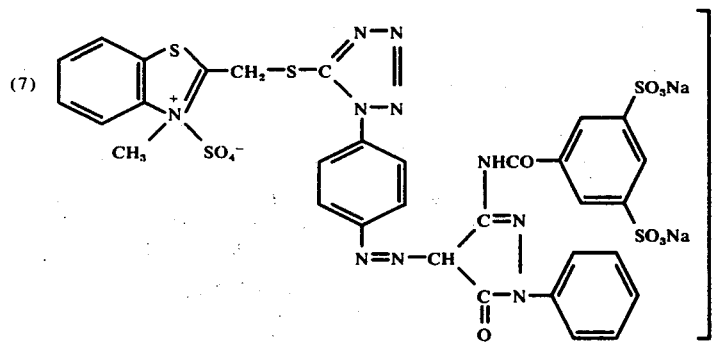
(8) 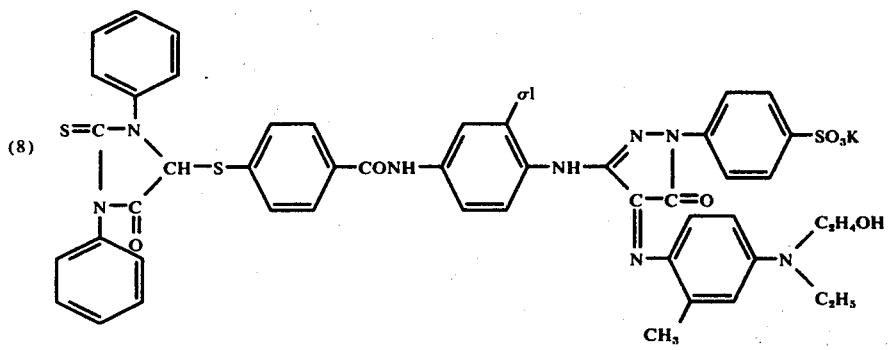
(9) 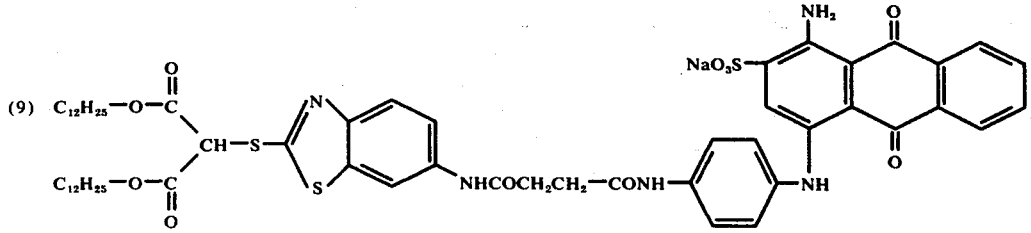

(10) 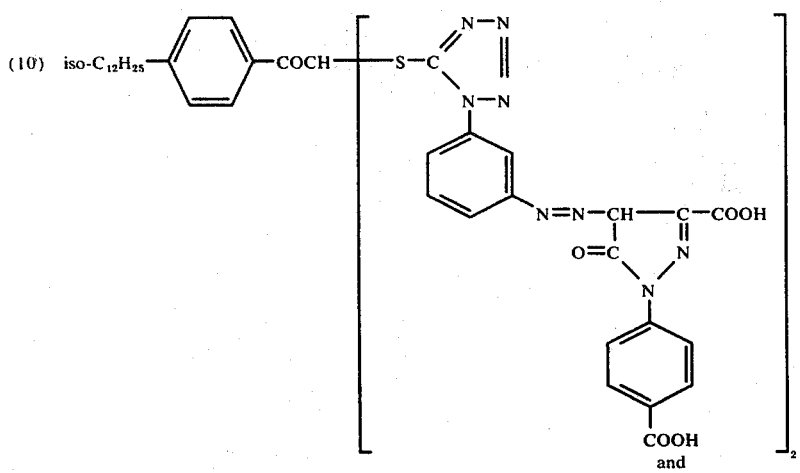

and

(11) 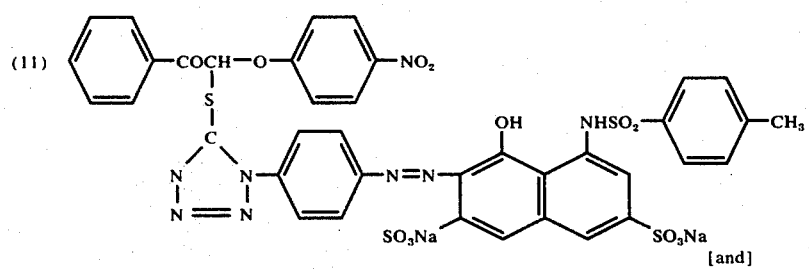

[and]

(12) 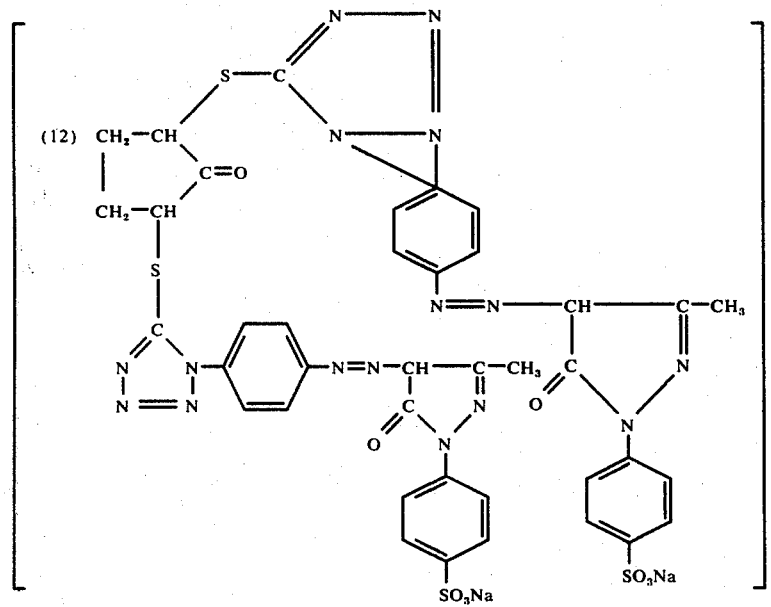

5. In a diffusion transfer process which comprises imagewise exposing a photosensitive material comprising a support and a silver halide photosensitive layer thereon containing silver halide grains and further comprising a dye image forming substance therein; devloping the exposed photosensitive material in an aqueous developing solution in the presence of a color developing agent thereby to form a diffusible dye image corresponding to the imagewise exposure and derived from the dye image forming substance; and transferring the dye image from the photosensitive material to an image receiving layer superposed on the photosensitive material at least during the development whereby the dye image corresponding to the imagewise exposure is obtained in the image receiving layer, the improvement with comprises, as the dye image forming substance, a diffusible-dye releasing type dye represented by the formula:

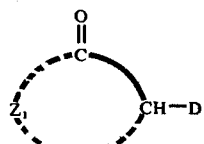

in which D represents a dye residue carrying a water-soluble radical, and $Z_1$ represents a group consisting of atoms forming a 5–7 membered carbon-cyclic or heterocyclic ring, the diffusible-dye releasing type dye per se being non-diffusible and capable of coupling with the color developing agent in the aqueous developing solution in the presence of the exposed silver halide to split off D in the formula whereby the dye image is produced from D so split off, and the compound produced upon splitting off D being substantially colorless.

6. A diffusion transfer process of claim 5, in which a molar ratio of the silver halide and the diffusibledye releasing type dye ranges from about 1: 0.07 to about 1: 0.7.

7. A diffusion transfer process of claim 5, in which a molar ratio of the silver halide and the diffusible-dye releasing type dye ranges from about 1: 0.1 to about 1 : 0.4.

8. In a direct positive process which comprises imagewise exposing a photosensitive material comprising a support and a silver halide photosensitive layer thereon containing silver halide grains and further comprising a dye image forming substance therein; developing the exposed photosensitive material in an aqueous developing solution in the presence of a color developing agent thereby to form a dye image corresponding to the imagewise exposure and derived from the dye image forming substance; and bleaching and fixing the developed photsensitive material, the improvement which comprises, as the dye image forming substance, a diffusible-dye releasing type dye represented by the formula:

$$R-\underset{Y}{\underset{|}{CH}}-D$$

in which D represents a dye residue carrying a water-soluble radical; Y represents hydrogen, halogen, an alkyl radical, an aryl radical, a heterocyclic radical, $-O-R_1$ or $-COOR_3$; $R_1$ is an alkyl radical, an aryl radical, a heterocyclic radical, an acyl radical or $-SO_2-R_2$; $R_2$ is an alkyl, aryl or heterocyclic radical; $R_3$ is an alkyl radical; R represents $-CO-R_4$,

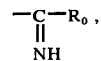

$-SO_2-R_5$, $-SO-R_5$, $-CN$ or $-N(R_6)_3$; $R_4$ is hydrogen, hydroxyl, $-R_O$, $-OR_O$, $-N(R_O)_2$, $-NH_2$ or $-NHR_O$; $R_5$ is hydrogen, $-R_O$, $-OR_O$ or $-N(R_O)_2$; $R_6$ is hydrogen or $-R_O$; and $R_O$ is an aliphatic, aryl or heterocyclic radical, and when two or more $R_O$s are present in one radical, two of said $R_O$s can form together a nitrogen-containing heterocyclic ring, the diffusible-dye releasing type dye per se being non-diffusible and capable of coupling with the color developing agent in the aqueous developing solution in the presence of the exposed silver haklide to split off D in the formula whereby the dye image is produced from D so split off, and the compound produced upon splitting off D being substantially colorless.

9. A direct positive process of claim 28, in which a molar ratio of the silver halide and the diffusible dye releasing type dye ranges from about 1: 0.07 to about 1: 0.7.

10. A direct positive process of claim 8, in which a molar ratio of the silver halide and the diffusible dye releasing type dye ranges from about 1 : 0.1 to about 1: 0.4.

11. A direct positive process of claim 8, wherein said dye is selected from the group consisting of (1) 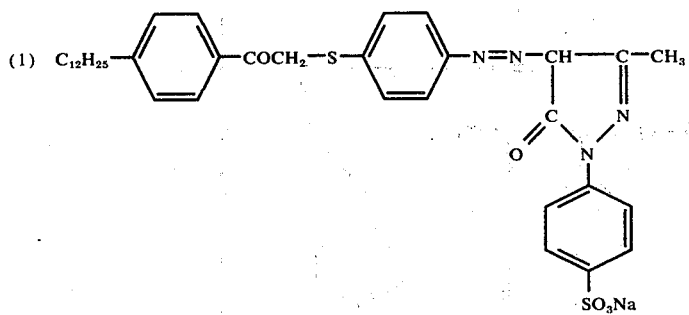

(2) 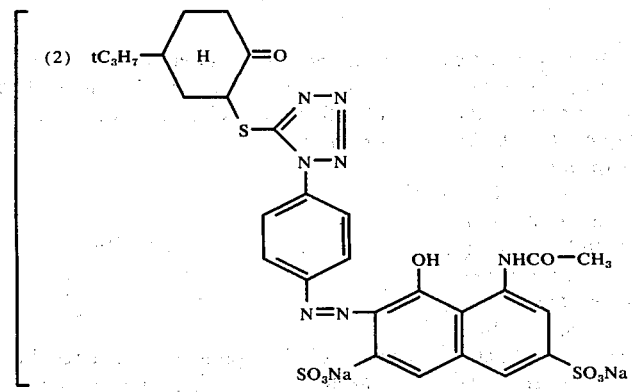

-continued
(3) 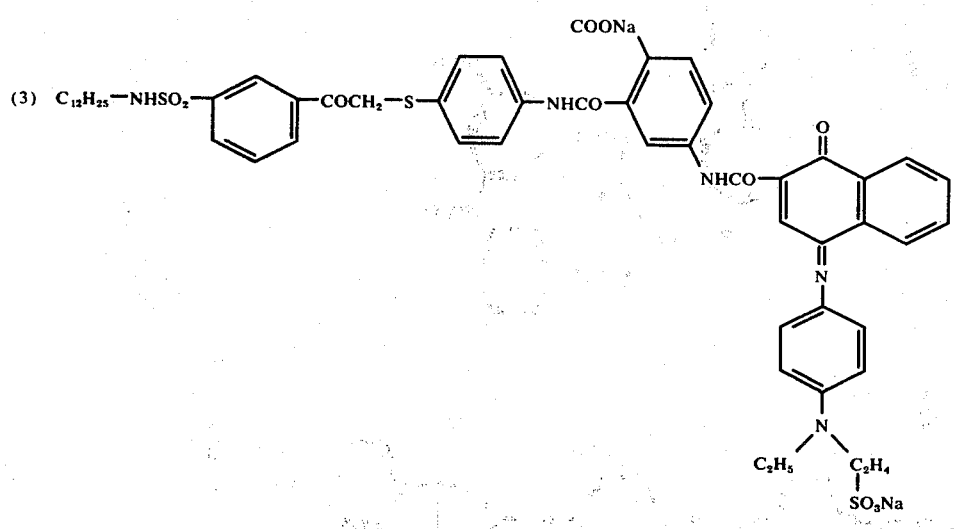
(4) 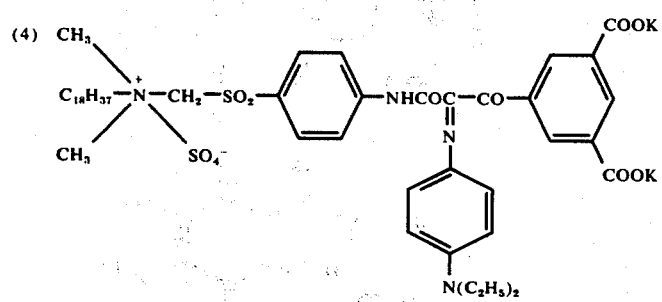
(5) 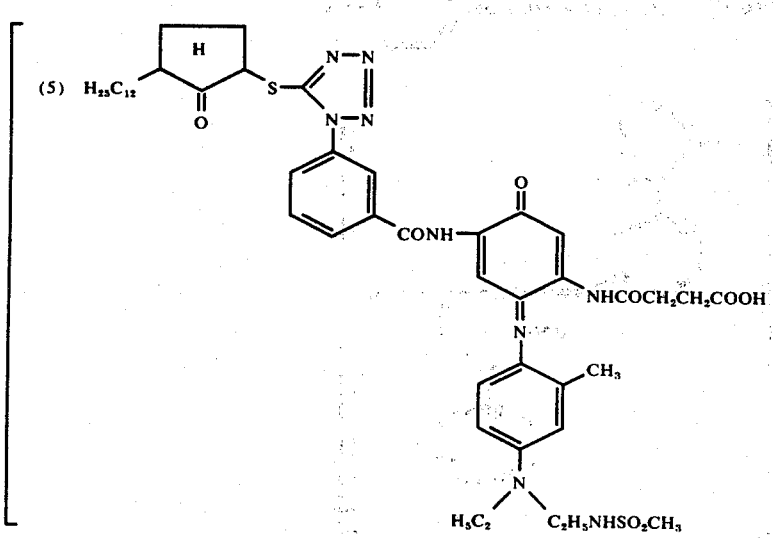
(6) 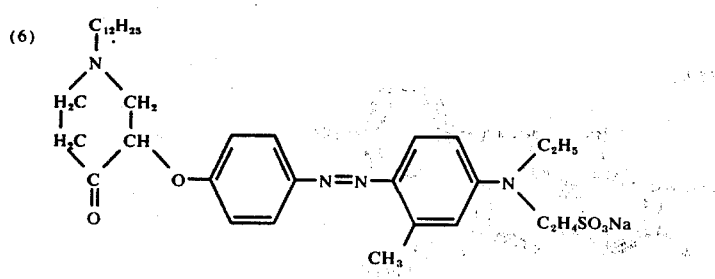

(7) 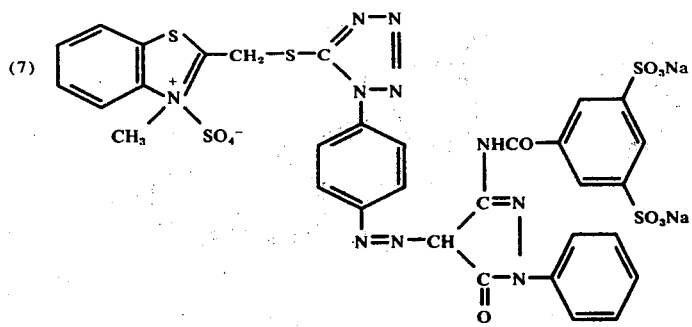
(8) 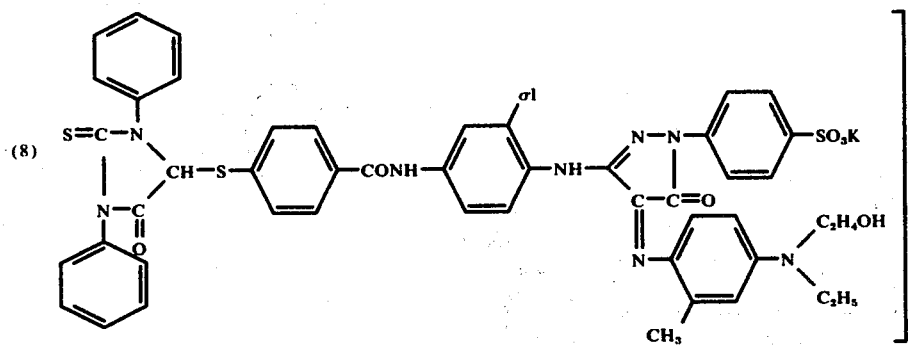
(9) 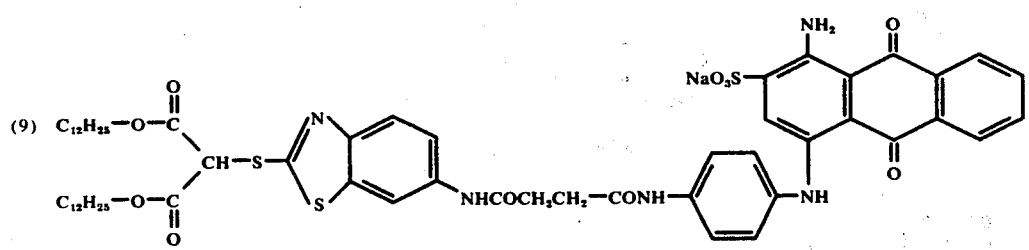
(10) 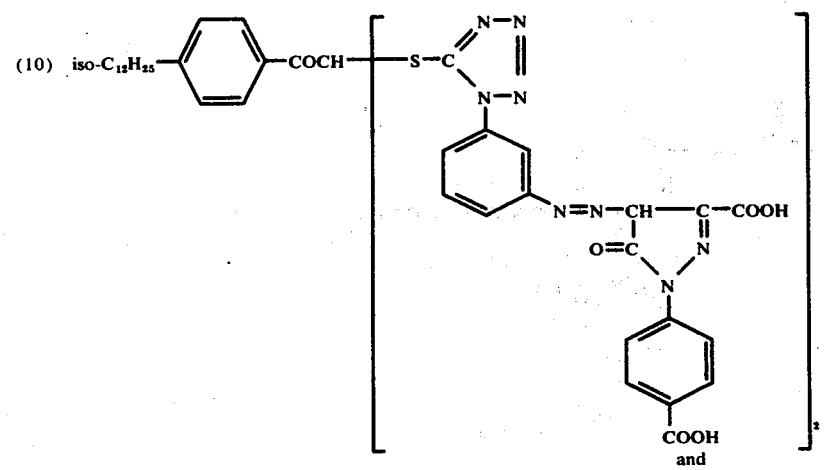
and
(11) 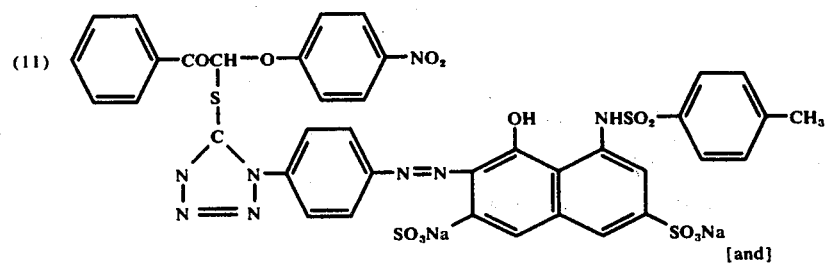
[and]

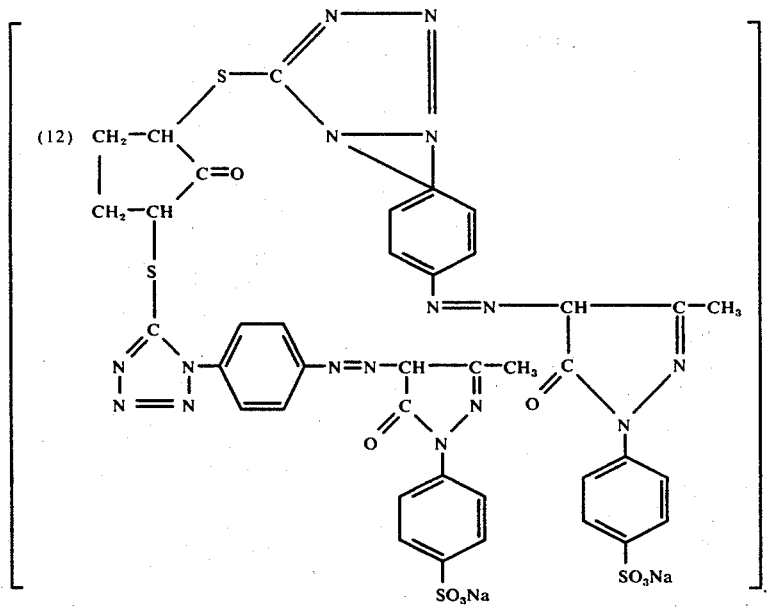

12. In a direct positive process which comprises imagewise exposing a photosensitive material comprising a support and a silver halide photosensitive layer thereon containing silver halide grains and further comprising a dye image forming substance therein; developing the exposed photosensitive material in an aqueous developing solution in the presence of a color developing agent thereby to form a dye image corresponding to the imagewise exposure and derived from the dye image forming substance; and bleaching and fixing the developed photosensitive material, the improvement which comprises, as the dye image forming substance, a diffusible-dye releasing type dye represented by the formula:

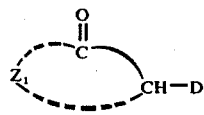

in which D represents a dye residue carrying a water-soluble radical, and $Z_1$ represents a group consisting of atoms forming a 5–7 membered carbon-cyclic or heterocyclic ring, the diffusible-dye releasing type dye per se being non-diffusible and capable of coupling with the color developing agent in the aqueous developing solution in the presence of the exposed silver halide to split off D in the formula whereby the dye image is produced from D so split off, and the compound produced upon splitting off D being substantially colorless.

13. A direct positive process of claim 12, in which a molar ratio of the silver halide and the diffusible dye releasing type dye ranges from about 1 : 0.07 to about 1 : 0.7.

14. A direct positive process of claim 12, in which a molar ratio of the silver halide and the diffusible dye releasing type dye ranges from about 1 : 0.1 to about 1: 0.4.

15. A diffusion transfer process of claim 1, in which the color developing agent is a p-phenylene diamine.

16. A diffusion transfer process of claim 1, in which the dye image forming substance is included in the silver halide photosensitive layer.

17. A diffusion transfer process of claim 5, in which the color developing agent is a p-phenylene diamine.

18. A diffusion transfer process of claim 5, in which the dye image forming substance is included in the silver halide photosensitive layer.

19. A diffusion transfer process of claim 5, wherein said dye is selected from the group consisting of:

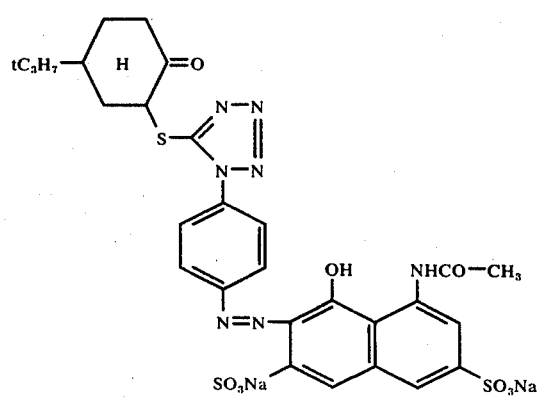

-continued
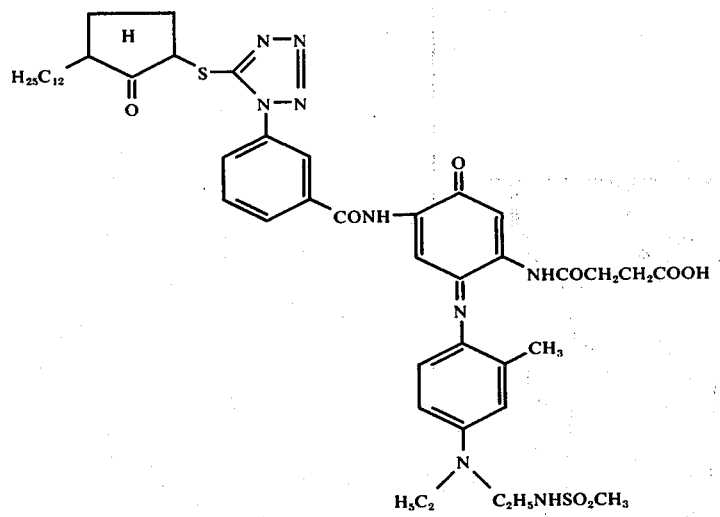
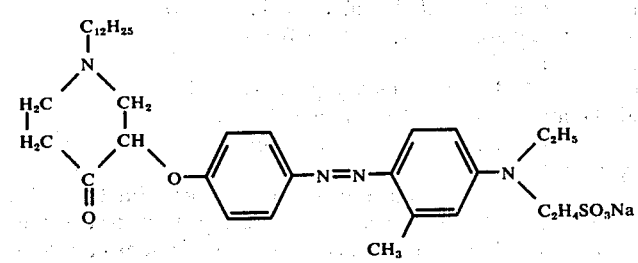
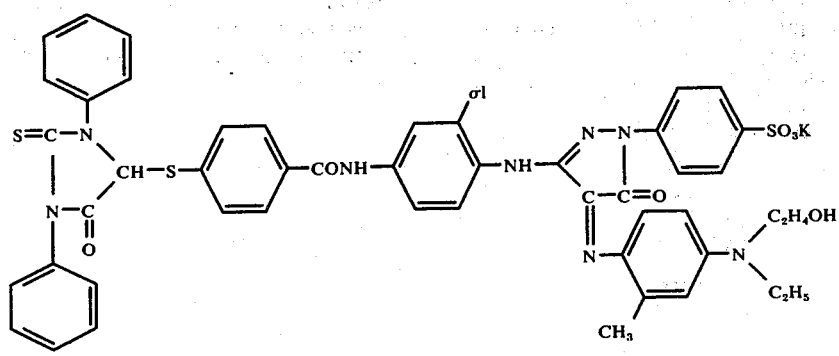
and

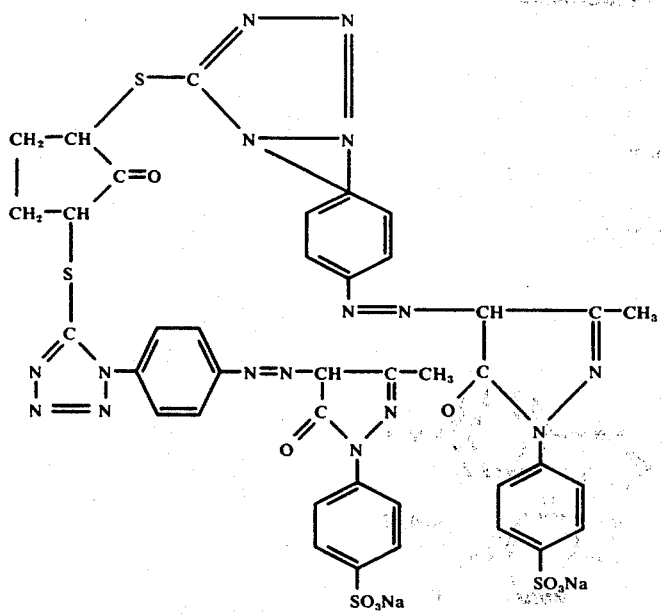

20. A direct positive process of claim 8, in which the color developing agent is a p-phenylene diamine.

21. A direct positive process of claim 8, in which the dye image forming substance is included in the silver halide photosensitive layer.

22. A direct positive process of claim 12, in which the color developing agent is a p-phenylene diamine.

23. A direct positive process of claim 12, in which the dye image forming substance is included in the silver halide photosensitive layer.

24. A direct positive process of claim 12, wherein said dye is selected from the group consisting of:

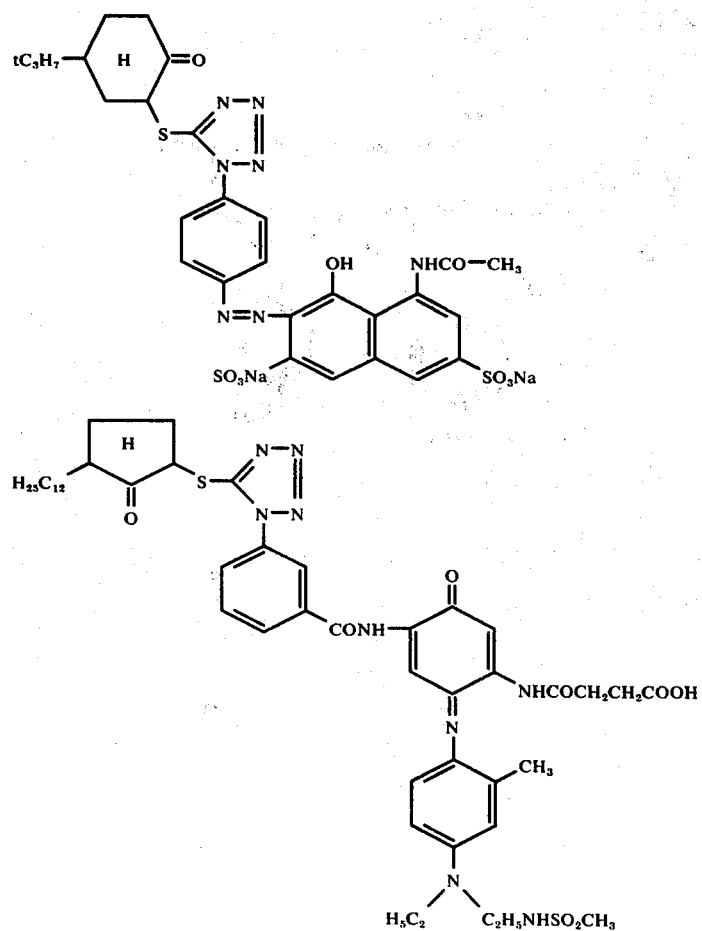

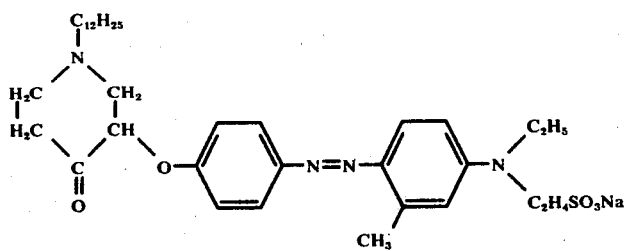
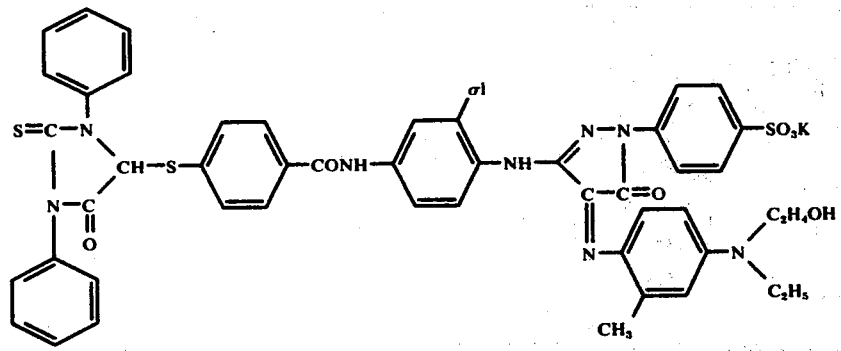
and
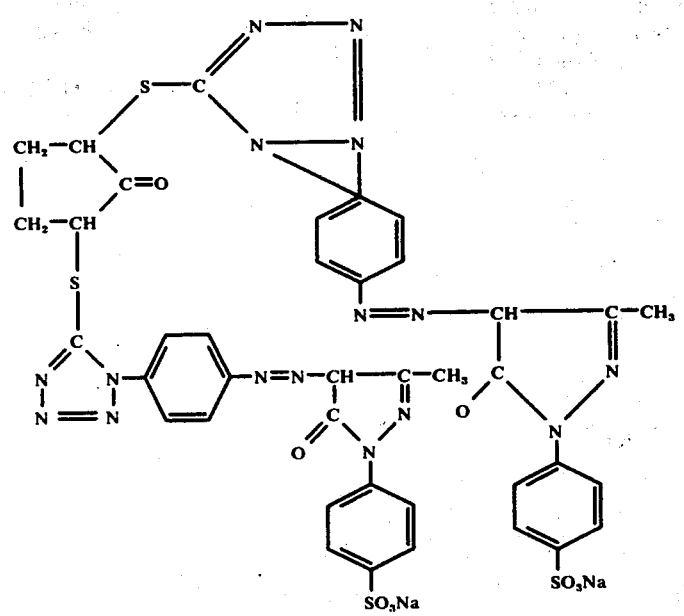

PAGE ONE OF TWO PAGES

UNITED STATES PATENT AND TRADEMARK OFFICE
CERTIFICATE OF CORRECTION

PATENT NO. : 4,029,503
DATED : June 14, 1977
INVENTOR(S) : MITSUTO FUJIWHARA et al It is certified that error appears in the above-identified patent and that said Letters Patent are hereby corrected as shown below:

Column 18, line 46: replace "shows" with --- showed ---.

Column 21, Claim 4: delete figure (2).

Columns 23-24, Claim 4: delete figures (5) through (8).

Column 25, Claim 4: delete "[and]".

Column 25, Claim 4: delete figure (12).

Column 28, line 23: (Claim 8) - replace "haklide" with --- halide ---.

Column 28, line 27: (Claim 9) - replace "28" with --- 8 ---.

Columns 27-28 and 29-30, Claim 11: delete figures (2) and (3).

Columns 29-30 and 31-32, Claim 11: delete figures (5) through (8).

Column 32, Claim 11: delete "[and]".

Columns 33-34, Claim 11: delete figure (12).

Column 33, line 30, Claim 12: after "therein", delete "the".

Column 37, last formula in Claim 19, and
Column 39, last formula in Claim 24 should appear as shown on the attached sheet.

UNITED STATES PATENT OFFICE
CERTIFICATE OF CORRECTION

Patent No. 4,029,503  Dated June 14, 1977

Inventor(s) MITSUTO FUJIWHARA et al.

It is certified that error appears in the above-identified patent and that said Letters Patent are hereby corrected as shown below:

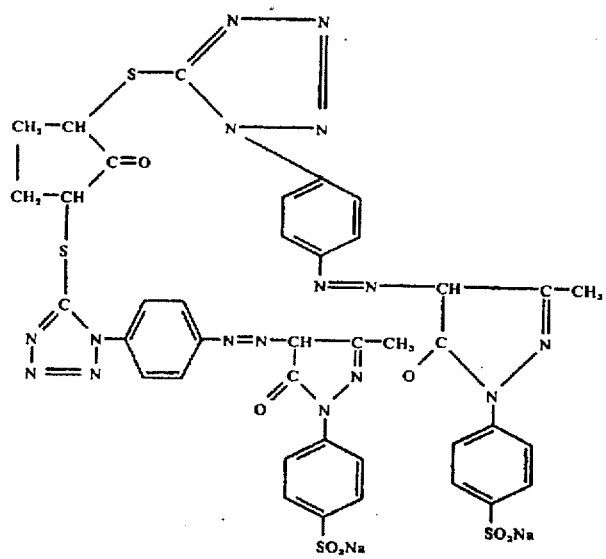

Signed and Sealed this

Tenth Day of January 1978

[SEAL]

Attest:

RUTH C. MASON
*Attesting Officer*

LUTRELLE F. PARKER
*Acting Commissioner of Patents and Trademarks*